(12) United States Patent
Zhang et al.

(10) Patent No.: US 8,640,727 B2
(45) Date of Patent: Feb. 4, 2014

(54) DOPANT GAS GENERATING DEVICE

(75) Inventors: Zhongxia Zhang, Beijing (CN); Hui Li, Beijing (CN); Yangtian Zhang, Beijing (CN); Jin Lin, Beijing (CN); Jianhua Liu, Beijing (CN)

(73) Assignee: Nuctech Company Limited, Beijing (CN)

( * ) Notice: Subject to any disclaimer, the term of this patent is extended or adjusted under 35 U.S.C. 154(b) by 254 days.

(21) Appl. No.: 12/743,926

(22) PCT Filed: Dec. 30, 2009

(86) PCT No.: PCT/CN2009/076239
§ 371 (c)(1),
(2), (4) Date: May 20, 2010

(87) PCT Pub. No.: WO2011/000196
PCT Pub. Date: Jan. 6, 2011

(65) Prior Publication Data
US 2011/0114210 A1    May 19, 2011

(30) Foreign Application Priority Data
Jun. 30, 2009   (CN) .......................... 2009 1 0088628

(51) Int. Cl.
*F17D 1/02*     (2006.01)
*G01N 27/62*    (2006.01)
*F16L 53/00*    (2006.01)

(52) U.S. Cl.
USPC ... 137/268; 137/205.5; 137/341; 137/599.12; 324/464

(58) Field of Classification Search
USPC ........ 137/76, 205.5, 268, 341, 564.5, 599.08, 137/599.11, 599.12, 599.13, 599.14, 137/599.15; 324/464, 465, 466
See application file for complete search history.

(56) References Cited

U.S. PATENT DOCUMENTS 3,668,382 A * 6/1972 Cohen et al. .................. 250/282
4,006,205 A * 2/1977 Etter ............................ 261/39.1
(Continued)

FOREIGN PATENT DOCUMENTS

CA     2 474 684 A1    8/2003
CN     201141852       10/2008
(Continued)

OTHER PUBLICATIONS

International Search Report for PCT/CN2009/076239 filed Dec. 30, 2009.
(Continued)

*Primary Examiner* — John Rivell
*Assistant Examiner* — Seth W Mackay-Smith
(74) *Attorney, Agent, or Firm* — Westman, Champlin & Koehler, P.A.

(57) ABSTRACT

The present invention relates to a dopant gas generating device for supplying the dopant gas to the ion mobility spectrometry instrument, comprising: a doping container; an air inlet having an inlet end connecting with an upstream side of a carrier gas passage and an outlet end connecting with the doping container; an air outlet having an entrance end connecting with the doping container and an exit end connecting with an downstream side of the carrier gas passage; a dopant gas generating unit for releasing the dopant gas, wherein the dopant gas generating unit is disposed within the doping container. Through disposing the dopant gas generating unit, which is used for releasing the dopant gas, within the doping container, the dopant gas in the present invention is applicable with not only a solid state dopant, but also a liquid state dopant.

6 Claims, 1 Drawing Sheet

(56) References Cited

U.S. PATENT DOCUMENTS

| | | | | |
|---|---|---|---|---|
| 4,555,347 A | * | 11/1985 | O'Dowd et al. | 210/752 |
| 5,053,343 A | * | 10/1991 | Vora et al. | 436/153 |
| 5,541,519 A | | 7/1996 | Stearns et al. | 324/464 |
| 5,968,837 A | | 10/1999 | Doring et al. | 436/173 |
| 6,109,543 A | * | 8/2000 | Bright et al. | 239/135 |
| 7,093,606 B2 | * | 8/2006 | Roberts | 137/14 |
| 7,347,219 B2 | * | 3/2008 | Gohde et al. | 137/613 |
| 7,497,968 B2 | * | 3/2009 | Ofer et al. | 252/299.01 |
| 2009/0166524 A1 | * | 7/2009 | Geraghty et al. | 250/282 |

FOREIGN PATENT DOCUMENTS

| | | |
|---|---|---|
| CN | 101382521 | 3/2009 |
| WO | WO 03018163 A1 * | 3/2003 |
| WO | WO2007042763 | 4/2007 |
| WO | WO2007148045 | 12/2007 |

OTHER PUBLICATIONS

Office Action from related Canadian Application No. 2,701,922, dated Aug. 1, 2011, 3 pgs.

Office Action from related Chinese Application No. 200910088628.0, dated Jun. 23, 2011, 5 pgs.

Office Action dated Oct. 29, 2010 issued by Canadian Patent Office for corresponding Canadian Application No. 2701922, 2 pgs.

Office Action dated Apr. 5, 2011 issued by Canadian Patent Office for corresponding Canadian Application No. 2701922, 2 pgs.

European Office Action for EP Serial No. 09 846 724.4, dated Jun. 19, 2013.

Communication pursuant to Article 94(3) EPC for European Patent Application No. 09 846 724.4-1559, dated Nov. 7, 2013, 5 pages.

* cited by examiner

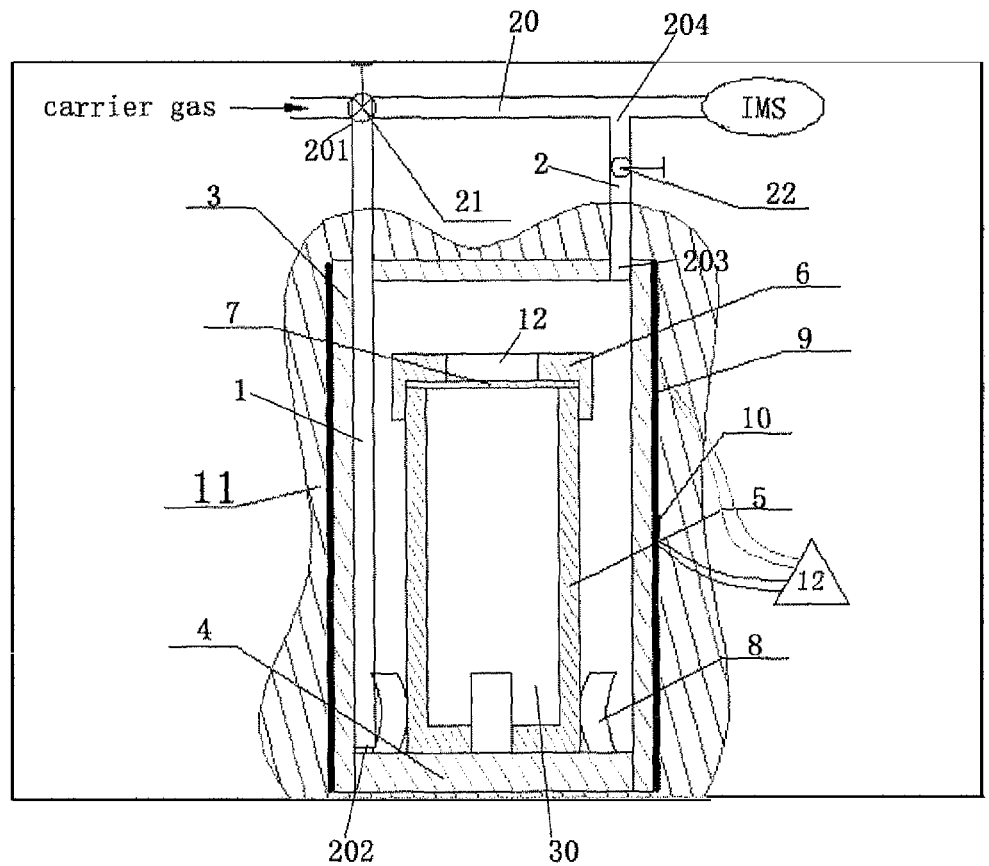

DOPANT GAS GENERATING DEVICE

FIELD OF INVENTION

The present invention relates to a dopant gas generating device in which both solid dopant and liquid dopant can be used, more particularly, to an adjustable dopant gas generating device which supplies gas with stable concentration to an ion mobility spectrometry instrument (IMS instrument), so that the inspection performance of the IMS instrument is improved.

BACKGROUND OF INVENTION

The ion migration spectrometry (IMS) is a rapid, sensitive and portable on site inspection technique. Such technique has already been applied in the military and security agencies, which can inspect toxic chemical agent, explosive and drugs and so on. In order to eliminate the interference and improve the inspection sensitivity, when the ion mobility spectrometry is used to inspect the contraband articles, it usually requires introducing a small amount of polychlorocarbon toward and into the ionized chamber of the migration tube, so that the polychlorocarbon is preferentially ionized under the action of the ion source. Thus, on one hand, it competes with the interference to reduce the ion concentration of the interference, accordingly, it helps to reduce the disturbance; on the other hand, it is able to transfer the ionic charge to the molecule of the article to be inspected, so that the ion concentration of the article to be inspected is greatly increased, thus the response signal of the article to be inspect, that is, the inspection sensitivity of the instruction is improved.

As a dopant substance, whether a liquid substance such as methylene chloride and the like or a solid substance such as hexachloroethane and the like, there is always a certain quantity of liquid molecules for keeping the balance with the dopant substance under the normal temperature and pressure (NTP), such molecules are the dopant gas to be used for improving the performance of the ion mobility spectrometry instrument. Apparently, different dopant substances, specifically, dopant substances in different states, contains the gaseous molecules with different concentration in the air under the same condition. In a general way, the vapor pressure of the liquid substances is much greater than the gas pressure volatilized from the substances in solid state. When the inspection items are different, the dopant to be used and the states thereof are different, and conditions for producing the dopant gas are different too. When the liquid dopant is used, the tightness of vessel for containing the dopant should be good. It shall be ensured that not only the dopant will be not overflowed and sprinkled during the usage and the operation of the device, but also the dopant gas can be produced smoothly and exuded in thimbleful. When the dopant in the solid state is used, it may also require heating the dopant to increase the production quantity of the dopant gas.

Presently, there is no dopant gas generating device meeting both of the above requirements well at the same time. Thus, it has been a demand to provide a dopant gas generating device, in which not only a solid state dopant, but also a liquid state dopant can be used, it also can adjust the generating quality of the dopant gas.

SUMMARY OF INVENTION

In view of the above, the present invention is made to overcome at least one aspect of the problems and shortages existing in the prior arts.

Accordingly, an object of present invention is to provide a dopant gas generating device in which both a solid dopant and a liquid dopant can be used.

Another object of the present invention is to provide a dopant gas generating device, which is able to control on/off operation and the doping quantity of the dopant gas.

In addition, the further object of the present invention is to provide a dopant gas generating device, which is able to easily achieve the replacement and the supplement of the dopant.

According to one aspect of the present invention, there is provided a dopant gas generating device for supplying dopant gas to an ion mobility spectrometry instrument, comprising a doping container, an air inlet pipe having an inlet end thereof connecting with an upstream side of a carrier gas passage, and an outlet end thereof connecting with the doping container; an air outlet pipe having an entrance end thereof connecting with the doping container and an exit end thereof connecting with a downstream side of the carrier gas passage; a dopant gas generating unit for releasing the dopant gas, wherein the dopant gas generating unit is disposed within the doping container.

Particularly, the dopant gas generating unit comprises: a bottle body; and a dopant disposed within the bottle body.

In one embodiment, the dopant is a solid state dopant; and the bottle body comprises a cover removably covering an upper opening of the bottle body, the cover is provided with small bores thereon to allow a gas volatilized from the solid state dopant to escape.

In another embodiment, the dopant is a liquid state dopant; a permeable membrane is provided on the upper opening of the bottle body, the permeable membrane can either prevent the liquid state dopant from leakage or allow the dopant gas to exude through the permeable membrane.

Preferably, the inlet end of the air inlet pipe is provided with a two-phase three-way solenoid valve; and the exit end of the air outlet is provided with a two-phase two-way solenoid valve.

Preferably, the outlet end of the air inlet pipe and the entrance end of the air outlet pipe substantially extend along the direction of the diagonal line of the bottle body.

Particularly, the outlet end of the air inlet pipe extends to a bottom portion of the bottle body; and the entrance end of the air outlet pipe extends out of an upper portion of the bottle body so as to be connected with the downstream of the carrier gas passage.

Further, a bottom cover removably connected to the doping container is provided at a lower end of the doping container, a frame for securing the bottle body is provided on the bottom cover.

Preferably, the dopant gas generating device further comprises a heating temperature control device comprising a heating membrane surrounding the circumferential wall of the doping container; a temperature sensor for detecting the temperature of the doping container; a temperature controller for controlling the temperature of doping container based on the temperature detected by the temperature controller; and a heat insulating layer for covering the outside of the heating membrane so as to seal the doping container.

Preferably, the bottle body and the cover are made of hard corrosion resistant material.

At least one aspect of the present invention takes advantages in following:

1. Through disposing the dopant gas generating unit, which is used for releasing the dopant gas, within the doping container, the dopant gas in the present invention is applicable with not only a solid state dopant, but also a liquid state dopant.

2. Both the air inlets and outlets of the doping container are provided with solenoid valve for controlling on/off operation of the feed of the dopant gas. The air inlet and air outlet on the doping container are located as far as possible so as to allow the flow to be able to sufficiently pass though the interior of the doping container.

3. The frame for securing the dopant bottle is installed on the bottom cover of the doping container, the bottom cover is connected with the doping container through threads, so that the dopant is easily to be replaced or supplemented.

4. By providing a heat temperature controlling device, the amount of the dopant gas can be adjusted though controlling the temperature of the temperature of the doping container so as to adjust the feed amount of the dopant gas, such that the performance of the ion mobility spectrometry instrument is greatly improved.

5. The bottle body and the cover are made of hard corrosion resistant material, the cover can be tighten up through a thread, a bore is provided at the middle of the cover, a permeable membrane is provided so as to either prevent the liquid state dopant from leakage or allow the dopant gas in minute quantities to exude through the permeable membrane.

BRIEF DESCRIPTION OF THE DRAWING

FIG. 1 is a structural schematic view of the dopant gas generating device according to an embodiment of the present invention.

DETAILED DESCRIPTION OF PREFERRED EMBODIMENTS

Preferred embodiments of the present invention will be described hereinafter in detail with reference to the attached drawings, wherein the like reference numerals refer to the like elements throughout the specification. The present invention may, however, be embodied in many different forms and should not be construed as being limited to the embodiments set forth herein; rather, these embodiments are provided so that the present disclosure will be thorough and complete, and will fully convey the concept of the invention to those skilled in the art.

FIG. 1 is a structural schematic view of the dopant gas generating device according to an embodiment of the present invention. Refer to FIG. 1, in which a dopant gas generating device for supplying dopant gas to an ion mobility spectrometry instrument is shown, the dopant gas generating device comprises a doping container 3; an air inlet pipe 1 having an inlet end 201 connecting with an upstream side of a carrier gas passage 20 and an outlet end 202 connecting with the doping container 3; an air outlet pipe 2 having an entrance end 203 connecting with the doping container 3 and an exit end 204 connecting with a downstream side of the carrier gas passage 20; a dopant gas generating unit including a dopant 30 and being used for releasing the dopant gas, wherein the dopant gas generating unit is disposed within the doping container 3. The carrier gas passage 20 is a flow passage for delivering the substances to be inspected into the ion mobility spectrometry instrument, for example, the carrier gas may be nitrogen or purified air. The carrier gas passage 20 routes from the left side of FIG. 1, i.e. an upstream side, to the right side of FIG. 1, that is, a downstream side.

As shown in FIG. 1, in particular, the dopant gas generating unit comprises a bottle body 5; and a dopant 30 disposed within the bottle body 5. The dopant may be a solid state dopant or a liquid state dopant. The bottle body 5 includes a cover 6 removably connected to an upper end thereof to seal an upper opening of the bottle body 5, when the dopant is under the solid state, the cover 6 is provided with small bores 12 to allow gas volatilized from the solid state dopant to escape. When the dopant is under the liquid state, a permeable membrane 7 is provided on the upper opening of the bottle body 5 so as to either prevent the liquid state dopant from leakage or allow the dopant gas to exude through the permeable membrane 7. The feed quantity of dopant gas can be changed by adjusting the bore diameter, membrane area and thickness on the cover 6.

Referring to FIG. 1, the inlet end 201 of the air inlet pipe 1 is provided with a two-phase three-way solenoid valve 21; at the same time, the exit end 204 of the air outlet 2 is provided with a two-phase two-way solenoid valve 22. Through above configuration, when the two-phase three-way solenoid valve 21 is powered on, it can switch off or on a flow branch flowing to the doping container 3. On the other hand, the exit end 204 of the air outlet pipe 2 is provided with the two-phase two-way solenoid valve 22, by adjusting the open ratio of the two-phase two-way solenoid valve 22, the flow branch passing through the doping container 3 is controlled to flow to the downstream side of the carrier gas passage 20 and the flow of the dopant gas also can be adjusted.

The outlet end 202 of the air inlet pipe 1 and the entrance end 203 of the air outlet pipe 2 substantially extend along the direction of the diagonal line of the bottle body 5. As shown in FIG. 1, the outlet end 202 of the air inlet pipe 1 extends to the bottom portion of the bottle body 5; and the entrance end 203 of the air outlet pipe 2 extends out of the upper portion of the bottle body 5 so as to be connected with the downstream of the carrier gas passage 20. Through locating the air inlet and air outlet on the doping container as far as possible so as to allow the flow to be able to sufficiently pass though the interior of the doping container, such that the doping efficiency is improved.

In one embodiment, referring to FIG. 1, a bottom cover 4 removably connected to the doping container 3 is provided at the lower end of the doping container 3, a frame 8 for securing the bottle body 5 is provided on the bottom cover 4. Through providing the frame 8, for example, an elastic piece as shown in FIG. 1, can secure the bottle body 5 on the bottom cover 6 so as to prevent the dopant, particularly the liquid state dopant from the leakage during the transportation and using process. However, the frame is limited to the embodiment shown in FIG. 1, but can be other embodiments.

Referring to FIG. 1, the dopant gas generating device further comprises a heating temperature control device, which comprises a heating membrane 9 surrounding the circumferential wall of the doping container; a temperature sensor 10 for detecting the temperature of the doping container; a temperature controller 12 for controlling the temperature of doping container based on the temperature detected by the temperature controller; and a heat insulating layer 11 for covering the outside of the heating membrane so as to seal the doping container. The heating membrane 9 can be a resistance wire or a print thick film heating element. The temperature sensor 10 can be a thermocouple or thermistor sensor and so on. The temperature sensor 12 may employ either a mechanic temperature controller or an electronic temperature controller, for example, a resistance temperature controller or a thermocouple temperature controller and the likes. The heat insulating layer 11 may employ such as glass-wool products, polyurethane foam or phenol formaldehyde foam and the likes. By providing a heat temperature controlling device, the feed amount of the dopant gas can be changed when the temperature of the doping container is changed.

Since most of the dopant gases, for example hydrochloric ether are corrosive, the bottle body 5 and the cover 6 are made of hard corrosion resistant material, for example, glass or stainless steel material and so on.

Although several exemplary embodiments of the present invention and its advantages have been described with reference to the appended drawings, it is noted that various changes, substitutions and alterations can be made herein without departing from the spirit and scope of the invention as defined by appended claims.

What is the claimed is:

1. A dopant gas generating device for supplying a dopant gas to an ion mobility spectrometry instrument, comprising:
   a doping container;
   an air inlet having an inlet end connecting with an upstream side of a carrier gas passage and an outlet end connecting with the doping container;
   an air outlet having an entrance end connecting with the doping container and an exit end connecting with an downstream side of the carrier gas passage;
   a dopant gas generating unit for releasing dopant gas, wherein the dopant gas generating unit is disposed within the doping container;
   further comprises a heating temperature control device comprising:
      a heating membrane surrounding a circumferential wall of the doping container;
      a temperature sensor for detecting the temperature of the doping container;
      a temperature controller for controlling the temperature of doping container based on the temperature detected by the temperature controller; and
      a heat insulating layer for covering the outside of the heating membrane so as to seal the doping container;
   said dopant gas generating unit comprises:
      a bottle body; and
      dopant disposed within said bottle body; and
   said bottle body comprises a cover removably covered an upper opening of the bottle body, said cover is provided with small bores thereon to allow a gas volatilized from the dopant to escape;
   a permeable membrane is provided on the upper opening of the bottle body, said permeable membrane can either prevent the dopant from leakage or allow the dopant gas to exude through the permeable membrane.

2. The dopant gas generating device according to claim 1, characterized in that, said inlet end of the air inlet pipe is provided with a two-phase three-way solenoid valve; and said exit end of the air outlet is provided with a two-phase two-way solenoid valve.

3. The dopant gas generating device according to claim 2, characterized in that, the outlet end of the air inlet pipe and the entrance end of the air outlet pipe substantially extend along the direction of the diagonal line of the bottle body.

4. The dopant gas generating device according to claim 3, characterized in that, the outlet end of the air inlet pipe extends to a bottom portion of the bottle body; and the entrance end of the air outlet pipe extends out of an upper portion of the bottle body so as to be connected with the downstream of the carrier gas passage.

5. The dopant gas generating device according to claim 1, characterized in that, a bottom cover removably connected to the doping container is provided at a lower end of the doping container, a frame for securing the bottle body is provided on the bottom cover.

6. The dopant gas generating device according to claim 1, characterized in that, the bottle body and the cover are made of hard corrosion resistant material.

* * * * *